US008781565B2

(12) United States Patent
Vartak et al.

(10) Patent No.: US 8,781,565 B2
(45) Date of Patent: Jul. 15, 2014

(54) DYNAMICALLY CONFIGURABLE BIOPOTENTIAL ELECTRODE ARRAY TO COLLECT PHYSIOLOGICAL DATA

(75) Inventors: Aniket A. Vartak, San Diego, CA (US); Robert S. Tartz, San Diego, CA (US); Mark S. Caskey, San Diego, CA (US)

(73) Assignee: QUALCOMM Incorporated, San Diego, CA (US)

(*) Notice: Subject to any disclaimer, the term of this patent is extended or adjusted under 35 U.S.C. 154(b) by 44 days.

(21) Appl. No.: 13/252,841

(22) Filed: Oct. 4, 2011

(65) Prior Publication Data

US 2013/0085367 A1    Apr. 4, 2013

(51) Int. Cl.
- A61B 5/04 (2006.01)
- A61B 5/00 (2006.01)
- A61B 5/0408 (2006.01)
- A61B 5/16 (2006.01)
- A61B 5/053 (2006.01)

(52) U.S. Cl.
CPC ............ *A61B 5/6898* (2013.01); *A61B 5/6844* (2013.01); *A61B 5/0006* (2013.01); *A61B 5/0408* (2013.01); *A61B 5/165* (2013.01); *A61B 2562/046* (2013.01); *A61B 5/0533* (2013.01)
USPC ........................................................ 600/513

(58) Field of Classification Search
USPC .................................. 600/509, 503, 393, 365
See application file for complete search history.

(56) References Cited

U.S. PATENT DOCUMENTS

| 5,261,747 A | 11/1993 | Deacutis et al. |
| 6,032,062 A | 2/2000 | Nisch |
| 6,326,936 B1 | 12/2001 | Inganas et al. |
| 7,233,684 B2 | 6/2007 | Fedorovskaya et al. |
| 2003/0088167 A1 | 5/2003 | Fendrock et al. |
| 2004/0039296 A1 | 2/2004 | Szopinski |
| 2006/0047187 A1 | 3/2006 | Goyal et al. |
| 2006/0057771 A1 | 3/2006 | Kovacs et al. |
| 2007/0027386 A1* | 2/2007 | Such et al. .................... 600/372 |
| 2007/0149876 A1 | 6/2007 | Mouradian et al. |

(Continued)

FOREIGN PATENT DOCUMENTS

| EP | 1278064 A1 | 1/2003 |
| EP | 1407713 A1 | 4/2004 |

(Continued)

OTHER PUBLICATIONS

Boucsein "Generalized Psychophysiological States" Electrodermal Activity, New York, Plenum Press, Sec. 3.2, 1992, pp. 260-292.

(Continued)

*Primary Examiner* — Paula J Stice
(74) *Attorney, Agent, or Firm* — Jeffrey D. Jacobs

(57) ABSTRACT

Methods, systems, and devices are described for collecting physiological data using a configurable biopotential array. The array is embedded on a surface area of a handheld device. The array includes a number of electrode tiles. The electrodes include biosensors to collect the physiological data of a user. The electrodes are polled to detect contact with the user's skin. Electrodes in contact with the skin are electrically coupled to form an active electrode area. The coupled electrodes collect the physiological data relating to the user via the biosensors. The electrodes are decoupled after contact with the user's skin is terminated. The physiological data is analyzed and an emotional state or health state of the user is determined from the analyzed data.

38 Claims, 11 Drawing Sheets

(56) References Cited

U.S. PATENT DOCUMENTS

| | | |
|---|---|---|
| 2007/0193887 A1 | 8/2007 | Tormoen et al. |
| 2008/0177190 A1 | 7/2008 | Libbus et al. |
| 2008/0235284 A1 | 9/2008 | Aarts et al. |
| 2009/0177144 A1 | 7/2009 | Masmanidis et al. |
| 2010/0036230 A1 | 2/2010 | Greene et al. |
| 2010/0041975 A1* | 2/2010 | Chen et al. .................. 600/393 |
| 2010/0086204 A1 | 4/2010 | Lessing |
| 2010/0123588 A1 | 5/2010 | Cruz et al. |
| 2011/0213268 A1 | 9/2011 | Kosaka et al. |
| 2012/0083675 A1 | 4/2012 | El Kaliouby et al. |
| 2012/0165622 A1 | 6/2012 | Rodríguez Ibáñez et al. |
| 2013/0317318 A1 | 11/2013 | Tartz et al. |

FOREIGN PATENT DOCUMENTS

| | | |
|---|---|---|
| EP | 1685794 A1 | 8/2006 |
| GB | 2378762 A | 2/2003 |
| WO | WO-2006090371 A2 | 8/2006 |
| WO | 2006131855 A2 | 12/2006 |
| WO | 2008017416 A2 | 2/2008 |
| WO | 2011022068 A1 | 2/2011 |
| WO | 2011094399 A2 | 8/2011 |

OTHER PUBLICATIONS

International Search Report and Written Opinion—PCT/US2012/058643—ISA/EPO—Jan. 7, 2013.

Russell "A Circumplex Model of Affect", Journal of Personality and Social Psychology, vol. 39, No. 6, 1980, pp. 1161-1178.

Sakurazawa, et al., "Entertainment Feature of a Game Using Skin Conductance Response," Proceedings of the 2004 ACM SIGCHI International Conference on Advances in computer entertainment technology [Online] 2004, pp. 181-186.

\* cited by examiner

DYNAMICALLY CONFIGURABLE BIOPOTENTIAL ELECTRODE ARRAY TO COLLECT PHYSIOLOGICAL DATA

BACKGROUND

Wireless communication systems are widely deployed to provide various types of electronic communication content such as voice, data, and so on. While electronic forms of communication (e.g., email, text messages, voicemail, phone calls) have enabled people to conveniently contact and interact with others, the richness of electronic communications is attenuated.

Electronic communications, by themselves, do not generally convey the full emotional state of the sender. For example, research suggests that 7% of emotional context in a given message is conveyed by the words (e.g., text in an electronic communications). Another 38% of the emotional context is conveyed vocally by the tone of the voice. The final 55% is expressed using non-verbal communication, such as facial expression and other body gestures (Mehrabian, Albert; Ferris, Susan R. (1967). "Inference of Attitudes from Nonverbal Communication in Two Channels". *Journal of Consulting Psychology* 31 (3): 248-252). With regards to electronic communications, the emotional context or emotional state of the sender is commonly misinterpreted by the receiver.

Biopotential electrodes may be used with biosensors to collect physiological data from the human body. The physiological data may be used to determine an emotional state of a person. In addition, the biosensors may be used to monitor the physical health of a person. The biosensor may convert a biological response into an electrical signal. Typically, these electrodes that include biosensors are a standard shape and size (e.g., 8 mm flat disc). The electrical signals generated from the biological response are relatively small. As a result, even a small amount of noise may significantly interfere with the electrical signal. This may cause the determined emotional or physiological state of the person to be inaccurate or unknown.

A biopotential electrode with a large surface area may increase the amount of noise that may cause interference with the electrical signals created by the biosensors. On the other hand, a biopotential electrode with too small of a surface area may render the reading of electrical signals associated with physiological data impractical.

SUMMARY

Methods, systems, and devices are described for collecting physiological data using a configurable biopotential array. In one example, the array is embedded on an external surface area of a handheld device. The array may include a number of electrode tiles that are associated with biosensors to collect the physiological data of a user. The electrodes may be polled to detect whether the electrodes are in contact with the user's skin. Electrodes that are in contact with the skin are electrically coupled to form an active electrode area. The biosensors associated with the coupled electrodes may collect the physiological data relating to the user. The coupled electrodes may be continuously polled to detect whether the contact with the user's skin is maintained. In addition, uncoupled electrodes in the array are continuously polled to detect contact. Coupled electrodes may be decoupled after contact with the user's skin is terminated. The collected physiological data may be analyzed and a state of the user may be determined from the analyzed data.

In one configuration, uncoupled electrode tiles in the array may be electrically coupled based on detecting contact to form a second active electrode area. Physiological data associated with the user may be collected via the coupled electrode tiles of the second active electrode area. In one example, a first active electrode area and the second active electrode area may exist nonconcurrently within the biopotential electrode array.

In one configuration, a determination may be made as to whether a minimum number of active electrode areas exist within the biopotential electrode array. Physiological data associated with the user may be collected based on the determination that the minimum number of active electrode areas exist.

In one example, a plurality of active electrode areas may be detected within the biopotential electrode array. Signal qualities associated with each of the plurality of active electrode areas may be compared. At least one of the plurality of active electrode areas may be selected to collected physiological data based on the comparison of signal qualities.

The biosensors associated with the electrode tiles may include an electrocardiogram sensor (ECG) or a galvanic skin response (GSR) sensor.

A communications device configured to collect physiological data using a dynamically configurable biopotential electrode array is also described. The device may include the biopotential electrode array, and a detection module configured to detect contact between at least two adjacent electrode tiles of the biopotential array and skin of a user. The device may further include a coupling module configured to electrically couple at least two adjacent electrode tiles, based on detecting contact. The coupled electrode tiles may form a first active electrode area within the biopotential electrode area. The device may also include a collection module configured to collect physiological data associated with the user via the coupled electrode tiles of the first active electrode area.

A system configured to collect physiological data using a dynamically configurable biopotential electrode array is also described. The system may include means for detecting contact between at least two adjacent electrode tiles of the biopotential electrode array and skin of a user. The system may further include means for electrically coupling at least two adjacent electrode tiles, based on detecting contact. The coupled electrode tiles may form a first active electrode area within the biopotential electrode array. The system may further include means for collecting physiological data associated with the user via the coupled electrode tiles of the first active electrode area.

A computer program product configured to collect physiological data using a dynamically configurable biopotential electrode array is also described. The product may include non-transitory computer-readable medium. The medium may include code to detect contact between at least two adjacent electrode tiles of the biopotential electrode array and skin of a user. The medium may further include code to electrically couple at least two adjacent electrode tiles, based on detecting contact. The coupled electrode tiles may form a first active electrode area within the biopotential electrode array. The medium may also include code to collect physiological data associated with the user via the coupled electrode tiles of the first active electrode area.

BRIEF DESCRIPTION OF THE DRAWINGS

A further understanding of the nature of the present invention may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

A configurable biopotential electrode array is described. The array may be used to collect physiological data about a user. In one example, the array may be embedded on a surface area of a device, such as a handheld electronic communications device. The array may include a number of electrode tiles (also referred to as "electrodes"). The electrodes may include biosensors that collect the physiological data of a user of the device. In one configuration, the electrodes (and their associated biosensors) may be activated to begin collecting the data when contact is detected between the electrodes and the skin of the user. The electrodes may be deactivated after contact between the electrodes and the skin of the user is terminated. A deactivated electrode may not collect the physiological data.

A contiguous area of a number of activated electrodes may function as a single electrode. The contiguous area may be referred to as an active electrode area (AEA). The electrodes within an AEA may collect physiological data of the user. The array may include one or more AEAs located at different positions along the array. For example, skin of the user may be in contact with a first group of electrodes (forming a first AEA) and a separate, second group of electrodes (forming a second AEA). The first AEA and the second AEA may not be adjacent to one another along the array. In addition, the first AEA and the second AEA may exist concurrently or nonconcurrently within the biopotential electrode array.

In one configuration, the electrodes of the array may be routinely polled to determine whether they are in contact with the skin of the user, or, if contact already exists, whether the contact between the skin of the user and the electrodes is maintained. The physiological data collected by the biosensors of the electrodes may be analyzed to determine an emotional state of the user or a health status of the user.

Thus, the following description provides examples, and is not limiting of the scope, applicability, or configuration set forth in the claims. Changes may be made in the function and arrangement of elements discussed without departing from the spirit and scope of the disclosure. Various embodiments may omit, substitute, or add various procedures or components as appropriate. For instance, the methods described may be performed in an order different from that described, and various steps may be added, omitted, or combined. Also, features described with respect to certain embodiments may be combined in other embodiments.

Figure 1:
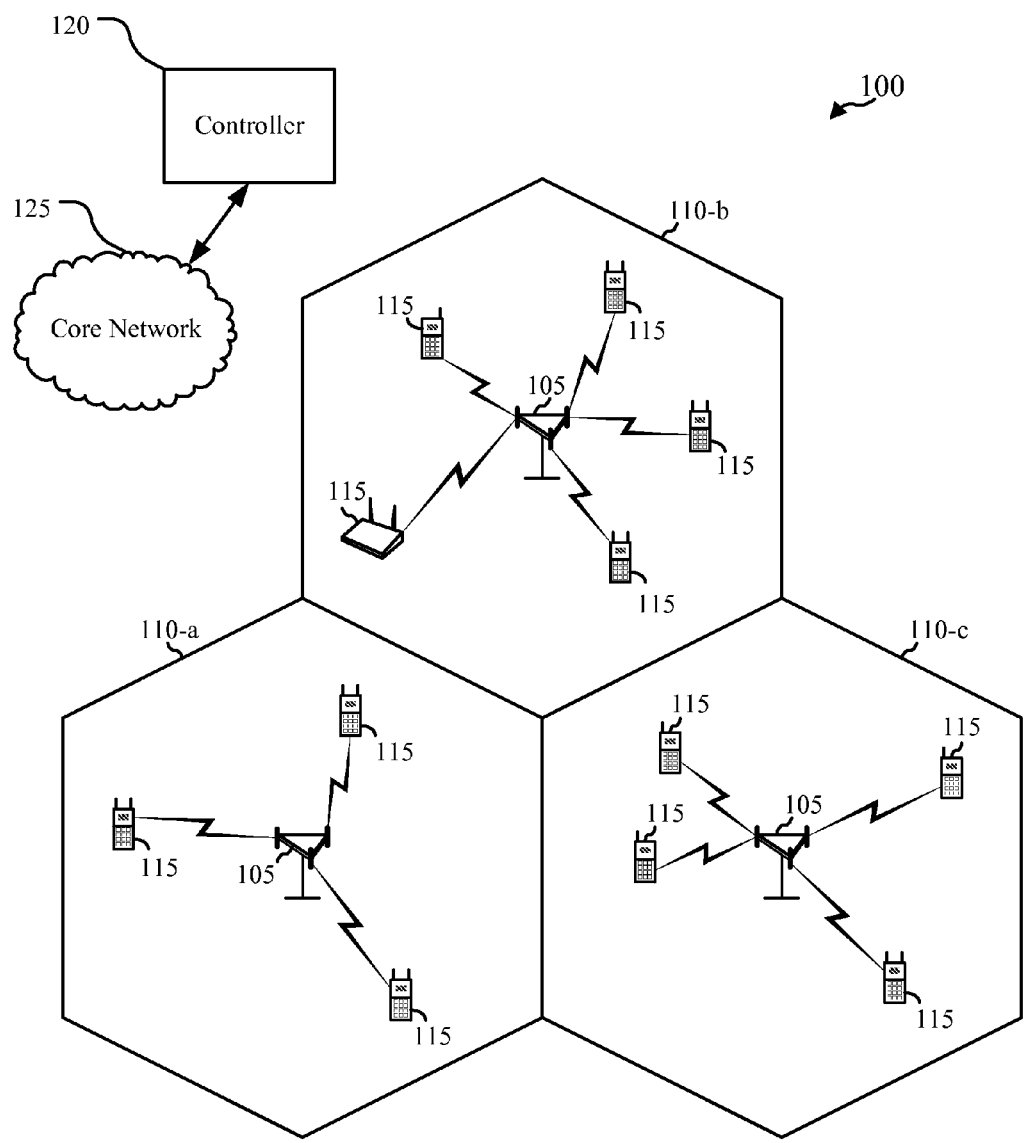
FIG. 1 shows a block diagram of a wireless communications system.

Referring first to FIG. 1, a block diagram illustrates an example of a wireless communications system 100. The system 100 includes base stations 105 (or cells), mobile devices 115, a base station controller 120, and a core network 125 (the controller 120 may be integrated into the core network 125). The system 100 may support operation on multiple carriers (waveform signals of different frequencies).

The base stations 105 may wirelessly communicate with the mobile devices 115 via a base station antenna (not shown). The base stations 105 may communicate with the mobile devices 115 under the control of the base station controller 120 via multiple carriers. Each of the base station 105 sites may provide communication coverage for a respective geographic area. The coverage area for each base station 105 here is identified as 110-*a*, 110-*b*, or 110-*c*. The coverage area for a base station may be divided into sectors (not shown, but making up only a portion of the coverage area). The system 100 may include base stations 105 of different types (e.g., macro, micro, and/or pico base stations). There may be overlapping coverage areas for different technologies.

The mobile devices 115 may be dispersed throughout the coverage areas 110. The mobile devices 115 may be referred to as mobile stations, mobile devices, access terminals (ATs), user equipments (UEs), subscriber stations (SSs), or subscriber units. The mobile devices 115 may include cellular phones and wireless communications devices, but may also include personal digital assistants (PDAs), other handheld devices, netbooks, notebook computers, etc.

The base stations 105 may allow users of the mobile devices 115 to communicate with each other. For example, a mobile device 115 may send electronic communications (e.g., email, text message, voicemail messages, etc.) to another mobile device. Users of different mobile devices 115 may also engage in real-time conversations (i.e., phone calls) using their respective devices. The mobile devices 115 may each include a configurable biopotential array of electrode tiles. The electrode tiles may be arranged in the array in different configurations and with different shapes. The array may be embedded along a surface area of the devices 115. Biosensors may be incorporated with the electrodes to collect physiological data associated with a user. Electrodes that are in contact with the skin of the user may be activated to begin collecting the data. For example, as the user holds the mobile device 115 in his/her hand, the electrodes in contact with the skin of the user's hand, fingers, etc. may be activated. Activated electrodes may be deactivated after contact with the user's skin has terminated. For example, as the user changes the position of his/her grip of the device 115, the electrodes that are currently activated may be deactivated, and the electrodes that are currently deactivated may be activated. The configurable biopotential array of electrode tiles described herein may be implemented on devices in other types of systems, as well.

Figure 2:
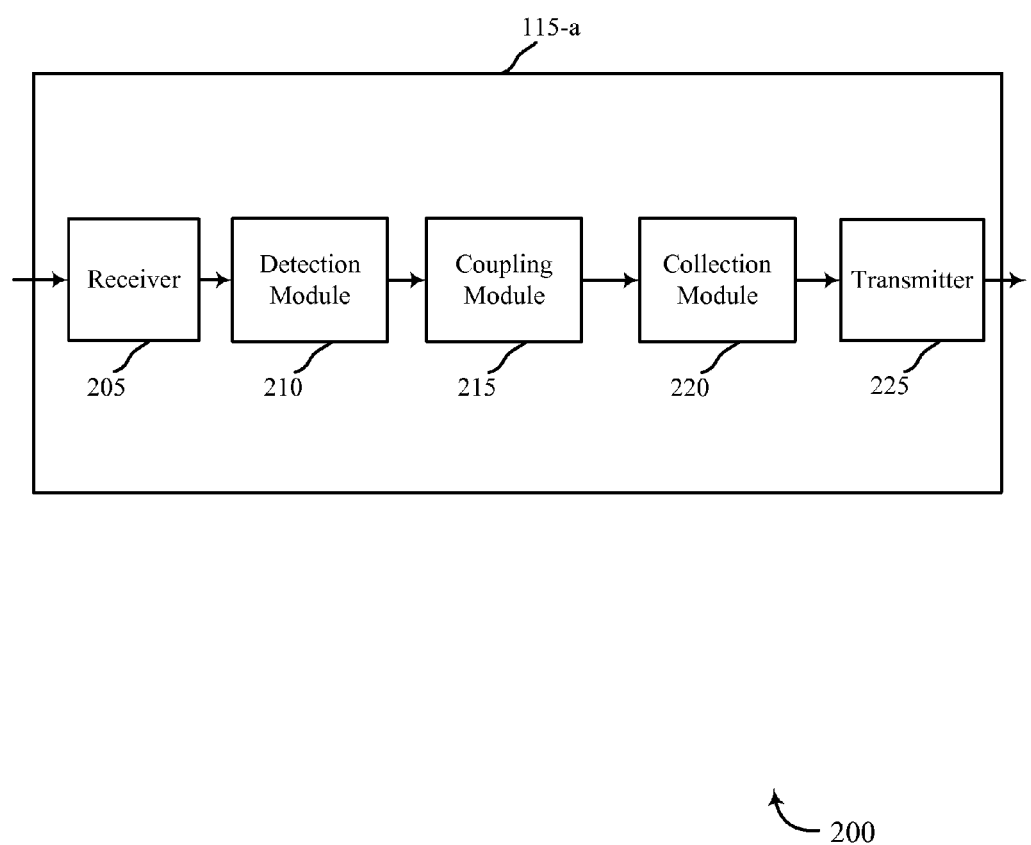
FIG. 2 is a block diagram illustrating one example of a mobile device.

FIG. 2 is a block diagram illustrating one example of a mobile device 115-a. The mobile device 115-a may be an example of the mobile devices 115 of FIG. 1. In one configuration, the mobile device 115-a may include a receiver 205, a detection module 210, a coupling module 215, a collection module, and a transmitter 225. The receiver 205 may receive signals and electronic communications from other devices, such as the base stations 105 or other mobile devices 115. The receiver 205 may also receive signals relating to possible contact between the skin of the user of the device 115-a and a surface area of the device 115-a. In one example, the detection module 210 may analyze the signals relating to the possible contact to determine whether contact exists between the user's skin and a particular surface area of the device 115-a. For example, the detection module 210 may detect contact between the skin of the user and a portion of a biopotential electrode array embedded on the surface area of the device 115. In other words, the detection module 210 may detect contact between the user's skin and at least two or more electrode tiles.

The coupling module 215 may couple the electrode tiles together that are detected to be in contact with the user's skin. For example, each electrode may be connected to the adjacent electrodes with an electronic switch. An example of the switch may include a field effect transistor (FET). When a particular electrode tile and at least one adjacent electrode tile comes in contact with the skin, the electronic switch between these two electrodes may be closed due to electrical conductive properties of the skin, thus creating a closed circuit between the electrodes. A closed circuit may activate the electrodes. The electronic switch between electrodes that are not in contact with the skin may not be closed, leaving an open circuit. These may be referred to as inactive electrodes.

The collection module 220 may collect data gathered from the activated electrodes. For example, the module 220 may collect physiological data associated with the user. This data may be gathered via biosensors incorporated with the electrode tiles. As a result, electrodes that are active may collect the data, while inactive electrodes may not participate in gathering the physiological data of the user. The configuration biopotential array architecture described herein may minimize electrical noise since electrodes that are inactive (not in contact with the user's skin) are not actively collecting data.

Figure 3:
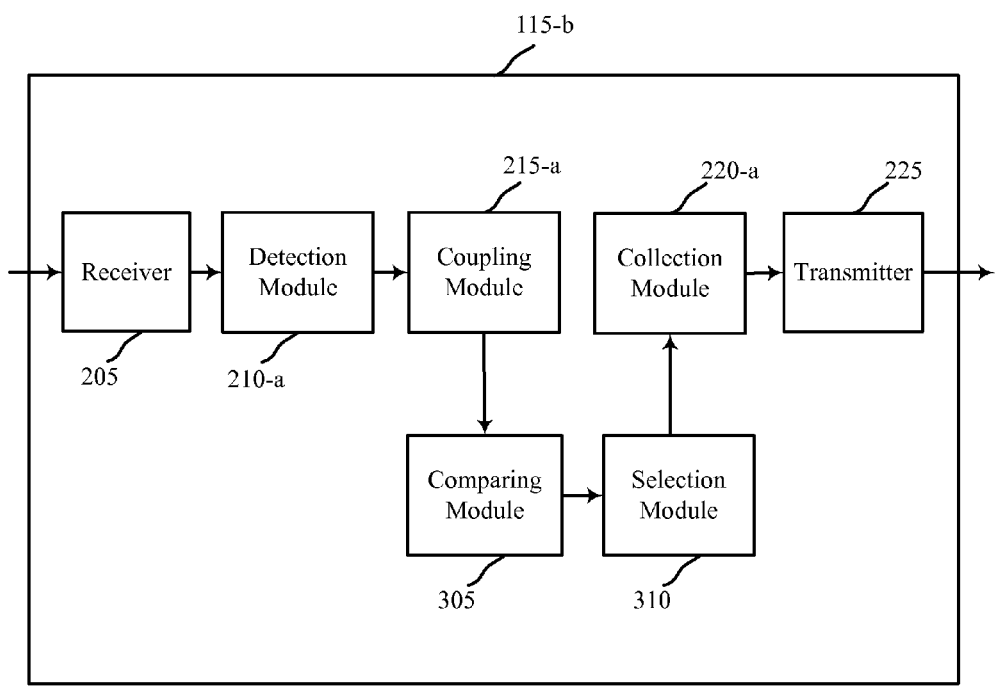
FIG. 3 is a block diagram illustrating another example of the mobile device.

Referring now to FIG. 3, a block diagram illustrates another example of a mobile device 115-b. The mobile device 115-b may be an example of the mobile device of FIG. 1 or 2. The device 115-b may include the receiver 205 and the transmitter 225, as previously described. The mobile device 115-b may also include a detection module 210-a, a coupling module 215-a, a collection module 220-a, a comparing module 305, and a selection module 310. The detection module 210-a may detect contact between a first group of electrode tiles embedded on an external portion of the device 115-b and the skin of a user of the device 115-b. The coupling module 215-a may electrically couple the first group of electrode tiles based on the detection module 210-a detecting contact. In one configuration, the first group of coupled electrode tiles may form a first AEA. In one example, the detection module 210-a may detect contact between the user's skin and a second group of electrode tiles. The coupling module 215-a may also electrically couple the second group of electrodes to form a second AEA. Each of the electrodes in the first AEA and the second AEA may include a biosensor that may begin collect data regarding the user of the device 115-b. In one example, the number of AEA may exceed a minimum number of AEAs needed to collect the data. The comparing module 305 may compare a signal quality metric associated with each AEA. For example, the comparing module 305 may compare the quality of the electrical signal detected from the skin of the user at each AEA. The selection module 310 may select which AEAs to receive data from based on the comparison of the signal quality metrics of each AEA. Examples of the signal quality metric may include, but is not limited to, a signal-to-noise ratio (SNR).

Figure 4:
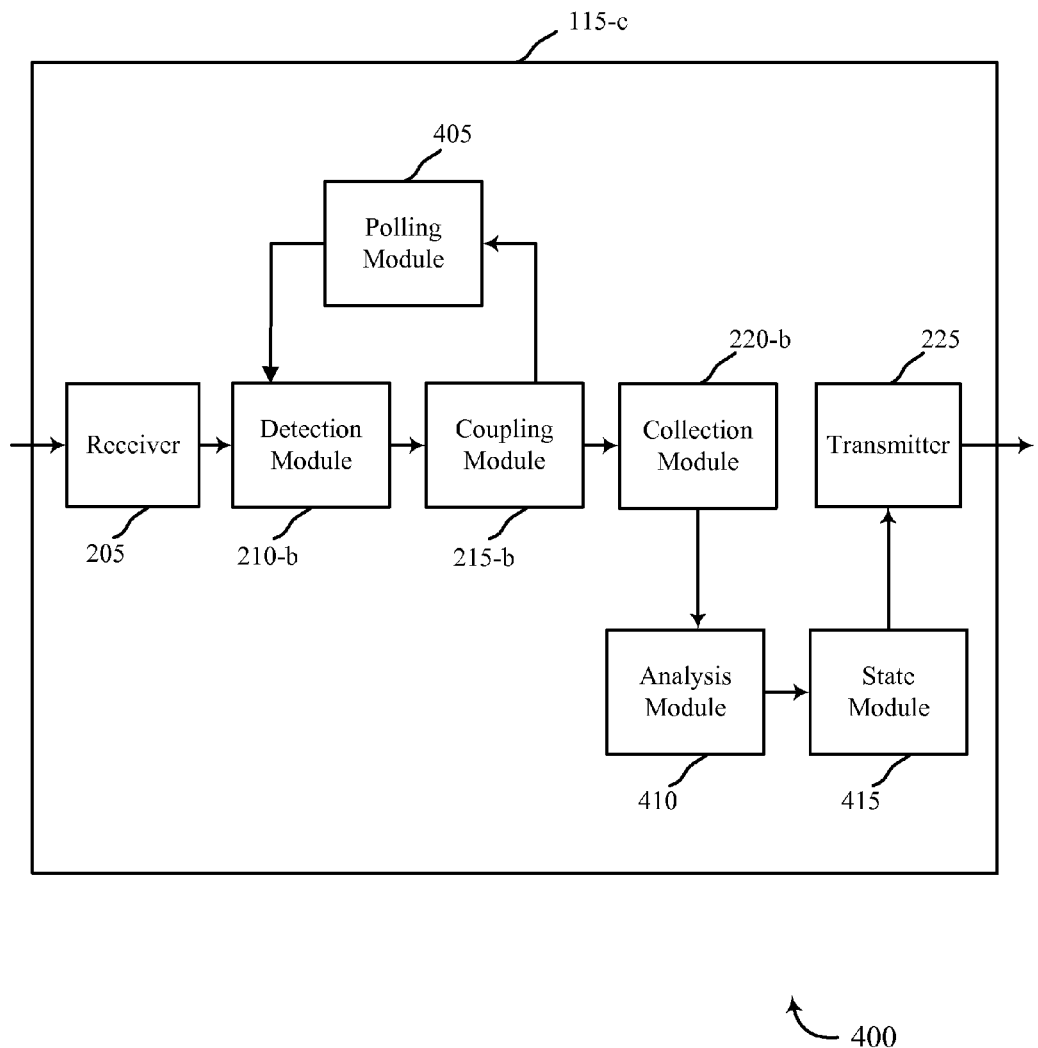
FIG. 4 is a block diagram illustrating a further example of the mobile device.

FIG. 4 is a block diagram illustrating a further example of a mobile device 115-c. The mobile device 115-c may be an example of the mobile device 115 of FIG. 1, 2, or 3. The device 115-c may include a receiver 205 and a transmitter 225, as mentioned above. The mobile device 115-c may also include a detection module 210-b, a coupling module 215-b, a collection module 220-b, a polling module 405, an analysis module 410, and a state module 415. In one example, the coupling module 215-b may electrically couple electrode tiles when the detection module 210-b detects contact between the electrodes and skin of a user.

In one configuration, the polling module 405 may routinely poll the coupled electrodes to determine whether the contact with the use's skin is maintained. An example of the polling module 405 may be a galvanic skin response (GSR) sensor. When skin contacts the electrodes, the current between the contacted electrodes may be greater than zero, due to the conductive properties of the skin. As a result, the polling module 405 may poll the flow of current between adjacent electrodes. If the flow of current between two polled electrodes is zero, the detection module 210-b may detect that the contact with the use's skin no longer exists. The coupling module 215-b may decouple the electrodes after the contact with the user's skin is terminated. The polling module 405 may also poll the flow of current between previously uncoupled electrodes to determine whether contact with the user's skin may exist. If the flow of current is greater than zero between at least two adjacent electrodes, the detection module 210-b may detect contact between these previously uncoupled electrodes and the skin of the user. The coupling module 220-b may then electrically couple these electrodes.

While coupled electrodes remain in contact with the user's skin, the collection module 220-b may collect physiological data of the user via biosensors associated with the electrodes. The analysis module 410 may analyze the collected physiological data. In one configuration, the state module 415 may determine a state of the user based on the analysis. For example, the state module 415 may determine an emotional state (e.g., happy, excited, sad, angry) for the user based on the analyzed physiological data. The state module 415 may also use the physiological data to determine the physical health of a person. An indicator that indicates the determined state of the user may be associated with an electronic communication (e.g., phone call, text message, email, voicemail, etc.). The transmitter 225 may transmit the electronic communication and the indicator to a recipient device. In one configuration, the transmitter 225 may transmit the indicator to an application that is used to monitor a person's health. A recipient (such as a doctor, nurse, or other healthcare provider) may access the indicator via the application to monitor the physical health of the person.

Figure 5:
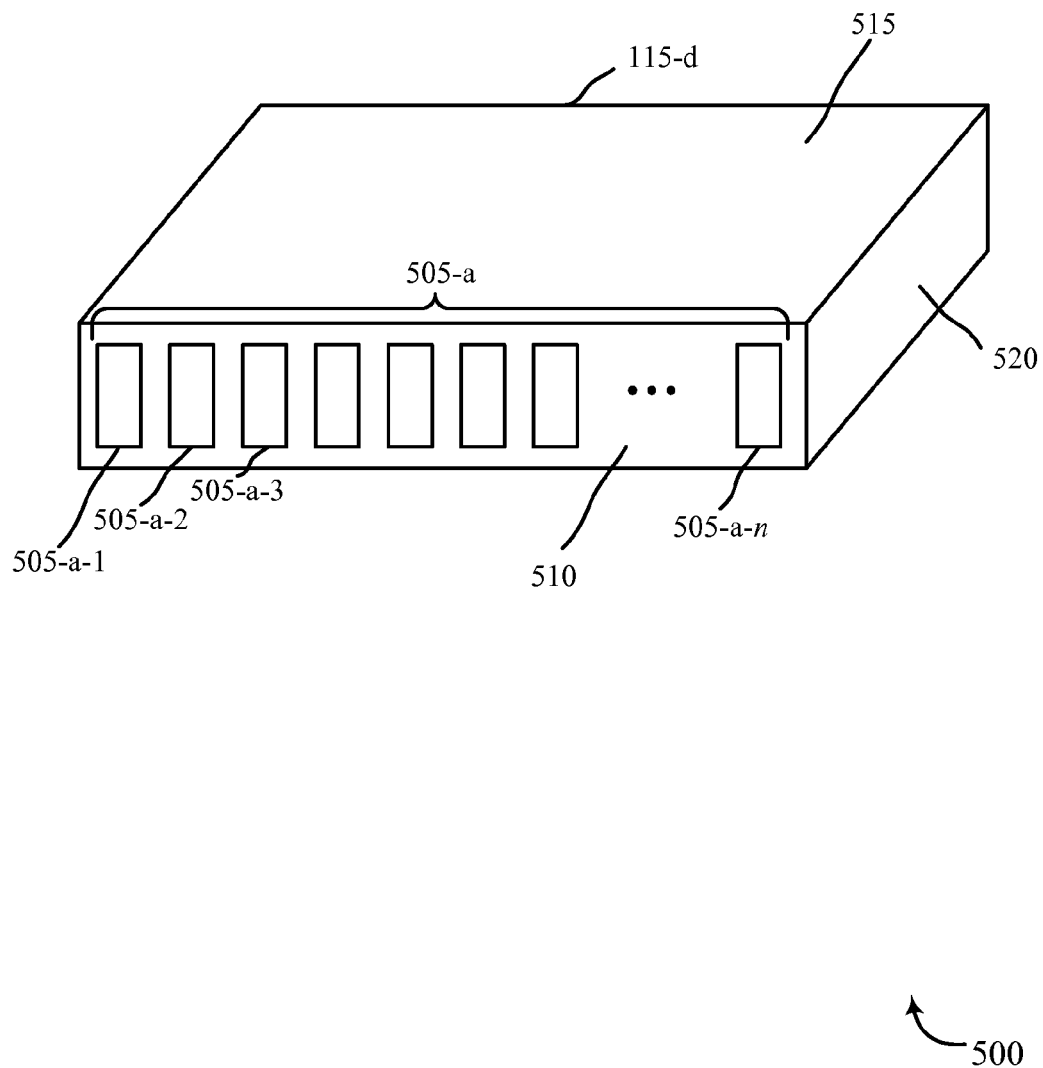
FIG. 5 a block diagram illustrates one example of a mobile device with a biopotential electrode array embedded on a surface area of the device.

Referring now to FIG. 5, a block diagram 500 illustrates one example of a mobile device 115-d with a biopotential electrode array 505-a embedded on a surface area of the mobile device 115-d. In one configuration, the mobile device 115-d may be an example of the mobile device 115 of FIG. 1, 2, 3, or 4. The device 115-*d* may include a number of surface areas. For example, a side surface area 510, a display surface area, and a bottom surface area 520. The array 505-*a* may be embedded on the side surface area 510 in this example. It is to be understood, however, that the array 505-*a* may be embedded on other surface areas of the mobile device 115-*d*. In one example, the biopotential array 505-*a* may include a number of electrode tiles 505-*a*-1-505-*a*-*n*. Each electrode 505-*a*-1-505-*a*-*n* may include a biosensor. Examples of biosensors may include an electrocardiogram (ECG) sensor a galvanic skin response (GSR) sensor, and other biopotential sensors. As illustrated, the electrode tiles 505-*a*-1-505-*a*-*n* may be rectangular in shape. A space may exist between each electrode. When current is detected flowing between adjacent electrodes due to contact with human skin, an electronic switch between the electrodes may be closed to create a closed circuit. The closed circuit may allow the electrodes to collect physiological data, while electrodes that are in an open circuit state (are not in contact with human skin) may not participate in collecting the data.

Figure 6:
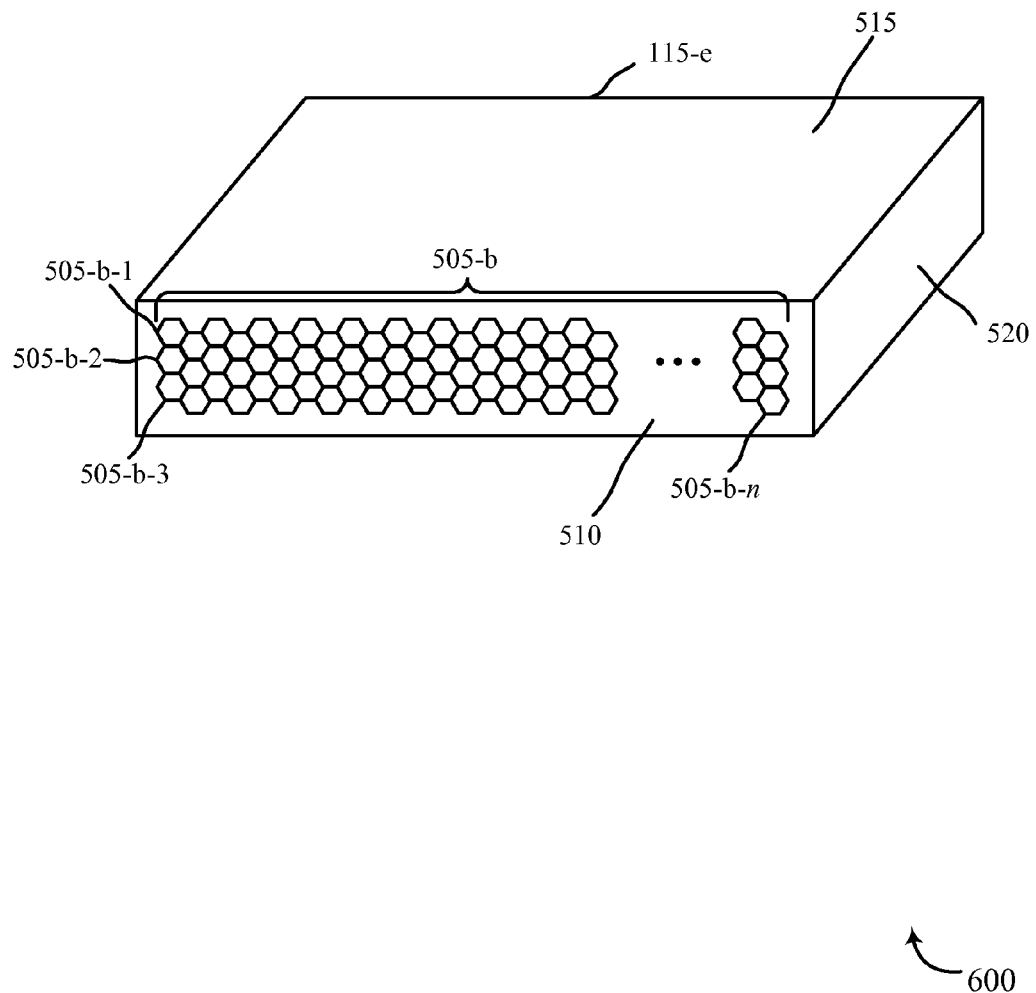
FIG. 6 is a block diagram illustrating another example of a biopotential array including electrode tiles embedded on a surface area of a mobile device.

FIG. 6, is a block diagram 600 illustrating another example of a biopotential array 505-*b* that includes electrode tiles 505-*b*-1-505-*b*-*n* embedded on a surface area of a mobile device 115-*e*. The mobile device 115-*e* may be an example of the mobile device 115 of FIG. 1, 2, 3, or 4. In one example, the device 115-*e* may include a side surface area 510, a display surface area 515, and a bottom surface area 520. The biopotential array 505-*b* may be embedded along the side surface area 510 in this example. The electrode tiles 505-*b*-1-505-*b*-*n* may be hexagonal in shape. As illustrated, a space may not exist between adjacent electrodes. Each electrode may include a biosensor to collect information about the user. The biosensors may begin to collect the data when their respective electrodes are in contact with the skin of a user.

Figure 7:
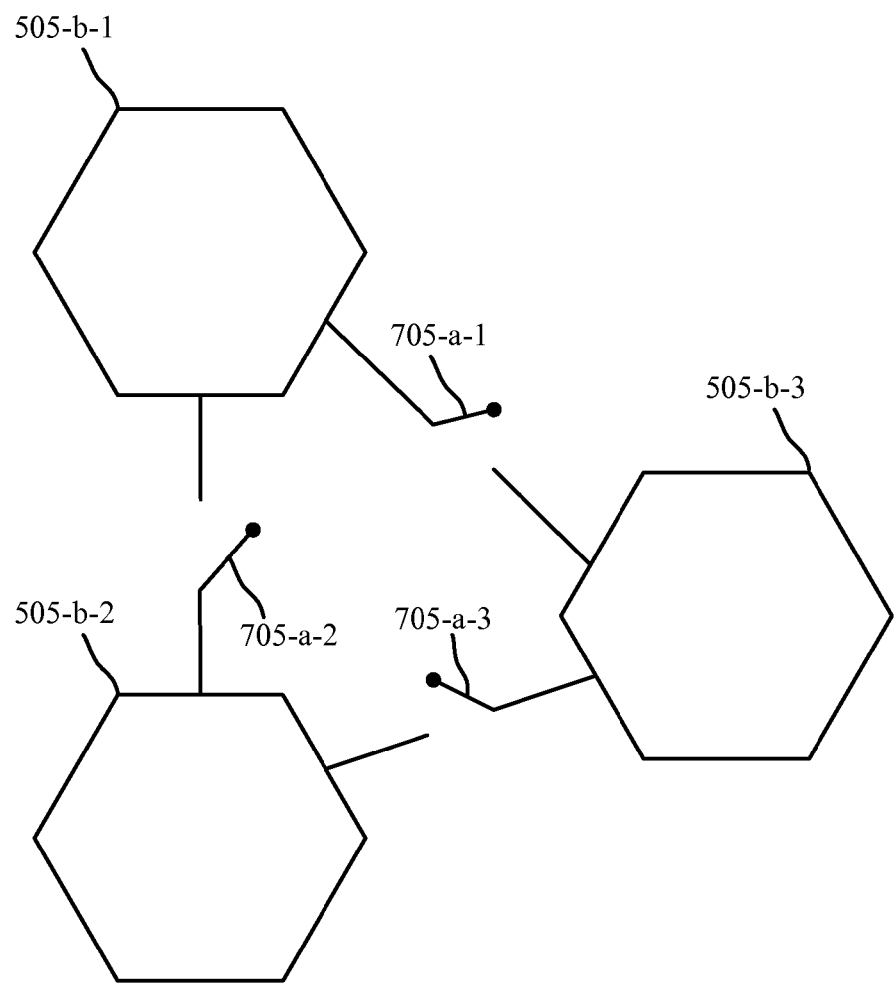
FIG. 7 illustrates an example of an electrode tile.

Referring now to FIG. 7, a collection 700 of electrode tiles 505-*b*-1, 505-*b*-2, 505-*b*-3 are illustrated. The electrode tiles may be examples of the electrodes of FIG. 5 or 6. In one example, an electronic switch 705-*a*-1, 705-*a*-2, and 705-*a*-3 may exist between each adjacent electrode tile. When the skin of a user contacts at least two adjacent electrodes, the electronic switch between the at least two electrodes may be closed due to the flow of current between the at least two adjacent electrodes. The biosensors associated with the at least two electrodes may begin to collect physiological data associated with the user. For example, the user may touch a first electrode tile 505-*b*-1 and a second electrode tile 505-*b*-2. When contact with the user's skin is detected, the electrodes may be electrically coupled by closing the electronic switch 705-*a*-2 between them. With the switch closed, the biosensors associated with the first and second electrodes 505-*b*-1, 505-*b*-2 may collect data about the user. The switch 705-*a*-2 may be opened (and the electrodes uncoupled) when contact between the electrodes and the skin is terminated.

Figure 8:
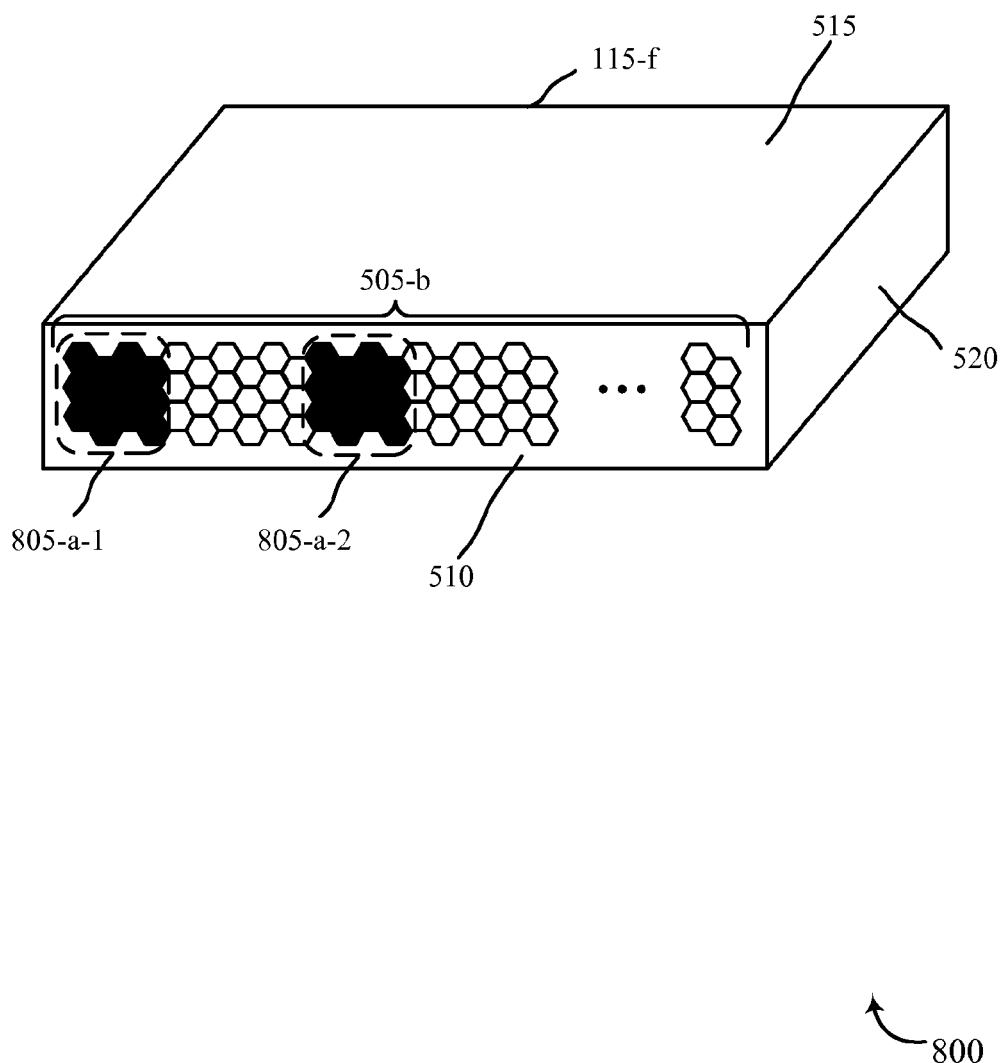
FIG. 8 is a block diagram illustrating a biopotential electrode array with a number of active electrode areas.

FIG. 8 is a block diagram 800 illustrating a biopotential electrode array 505-*b* embedded on a mobile device 115-*f* with a number of AEAs 805-*a*-1, 805-*a*-2. The mobile device 115-*f* may be an example of the mobile device 115 of FIGS. 1, 2, 3, 4, 5, of 6. In one configuration, the device 115-*f* may include a number of surface areas. For example, the device may include a display surface area 515, a bottom surface area 520, and a side surface area 510. In one example, the array 505-*b* may be embedded on the side surface area 510 of the mobile device 115-*f*. It is to be understood that the array 505-*b* may be embedded on other surface areas of the device in addition to, or in place of, the side surface area 510.

In one configuration, the array 505-*b* may include a first AEA 805-*a*-1 and a second AEA 805-*a*-2. Each AEA may include at least two electrode tiles that have been electrically coupled. In other words, each AEA may include electrode tiles that are in contact with the skin of a user. As the user's grip of the device 115-*f* shifts along the side surface area 510, the position of one or both AEAs may also change. For example, at a first time period, the user may be holding the device 115-*f* so that his/her skin is in contact with the electrodes in the first AEA 805-*a*-1 and the second AEA 805-*a*-2. The electrode tiles in these AEAs may collect physiological data associated with the user while they are activated (i.e., in contact with the user's skin). At a second time period, the user may change the position of his/her grip of the device 115-*f*. As a result, the user may no longer be in contact with the electrodes in the first AEA 805-*a*-1. These electrodes may be deactivated and the first AEA 805-*a*-1 may cease to exist. Physiological data may still be collected during the second time period via the electrodes of the second AEA 805-*a*-2, if the user continues to touch this portion of the array 505-*b*. If the user grips a previously untouched portion of the array 505-*b*, the electrodes in this portion may be coupled and a new AEA may be formed.

As illustrated in this example, the AEAs may be dynamically changed. For example, as the user shifts his/her grip on the side surface area 510 of the mobile device 115-*f*, the position and number of AEAs may also change. The polling module 405 may continuously poll the flow of current between adjacent electrodes to determine which contiguous areas remain active and which inactive areas of the array 505-*b* should be activated. This architecture allows the collection of the physiological data to occur while the user adjusts his/her grip on the device 115-*f* (as long as at least a portion of the skin is contacting the array 505-*b*).

Figure 9:
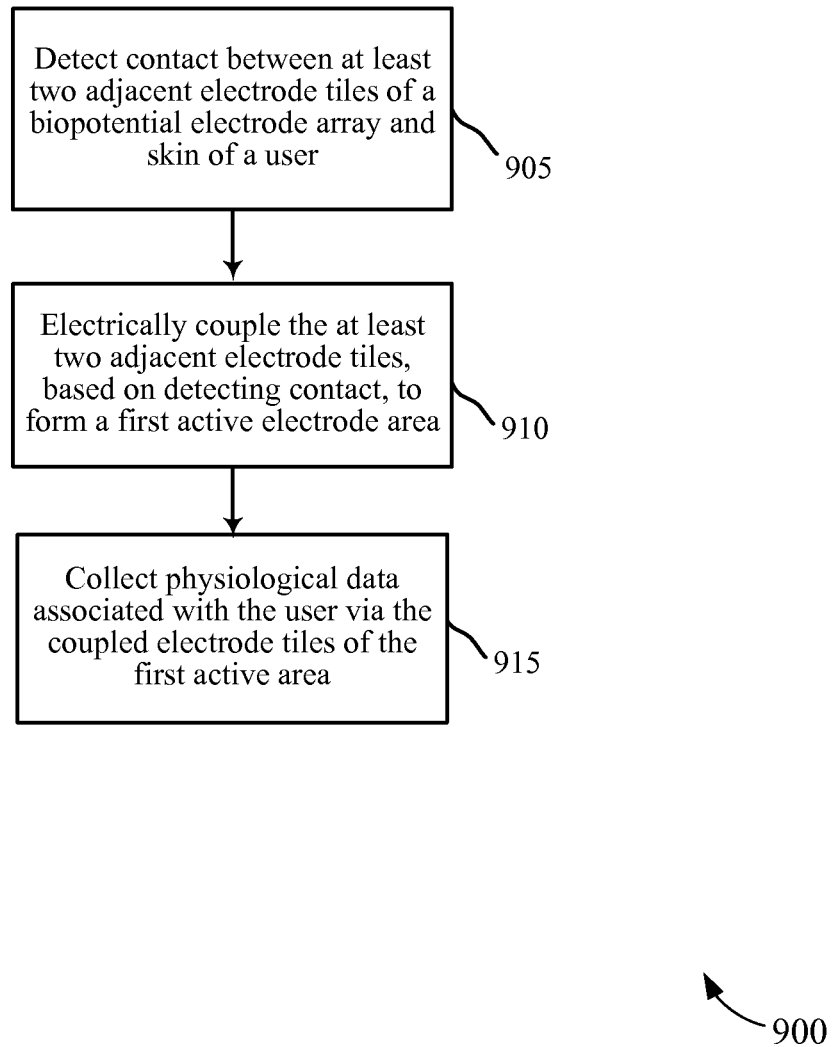
FIG. 9 is a flow chart illustrating one example of a method to collect physiological data using a dynamically configurable biopotential electrode array.

Referring now to FIG. 9, a flow chart is provided illustrating one example of a method 900 to collect physiological data using a dynamically configurable biopotential electrode array. The method 900 may be implemented by a mobile device, such as the mobile device 115 of FIG. 1, 2, 3, 4, 5, 6, or 8. In one configuration, the method 900 may be implemented by the detection module 210, the coupling module 215, and the collection module 220 of FIG. 2.

In one example, the biopotential electrode array may be embedded on a surface area of the mobile device 115. The array may include a number of electrode tiles. Each electrode may be associated with a biosensor to collect information about a user, such as physiological information. At block 905, contact between at least two adjacent electrode tiles of the biopotential electrode array and skin of a user may be detected. At block 910, the at least two adjacent electrodes may be electrically coupled when the contact is detected. For example, an electronic switch between the at least two adjacent electrodes may be closed when the user touches the electrodes. The electrically coupled electrodes may form a first AEA. At block 915, physiological data associated with the user may be collected via the coupled electrode tiles in the first AEA. Uncoupled electrodes in the biopotential electrode array may not participate in the collection of the physiological data associated with the user.

Therefore, the method 900 may provide for collecting physiological data using a dynamically configurable biopotential electrode array embedded on the mobile device 115. It should be noted that the method 900 is just one implementation and that operations of the method 900 may be rearranged or otherwise modified such that other implementations are possible.

Figure 10:
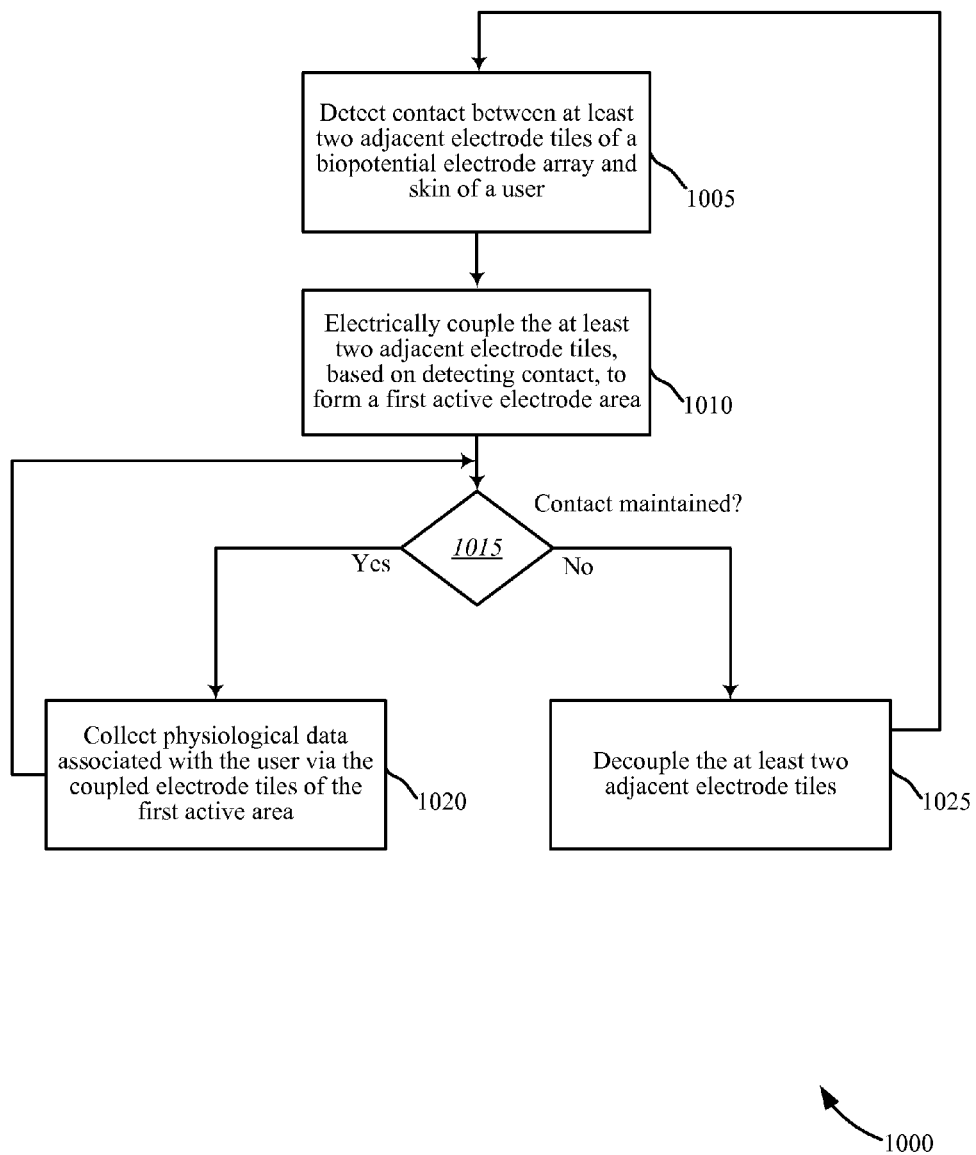
FIG. 10 is a flow chart illustrating one example of a method to determine whether to maintain an electric coupling of at least two electrode tiles within a configurable biopotential electrode array.

FIG. 10 is an example of a method 1000 to determine whether to maintain an electric coupling of at least two electrode tiles within a configurable biopotential electrode array.

The method 1000 may be implemented by a mobile device, such as the mobile device 115 of FIG. 1, 2, 3, 4, 5, 6, or 8. In one configuration, the method 1000 may be implemented by the detection module 210-*b*, the coupling module 215-*b*, the collection module 220-*b*, and the polling module 405 of FIG. 4.

In one example, the biopotential electrode array (including a number of electrode tiles) may be included on a external portion of the mobile device 115. At block 1005, contact between at least two adjacent electrode tiles and skin of a user may be detected. At block 1010, the at least two adjacent electrode tiles may be coupled when contact is detected. The coupled electrodes may form a first AEA. In one configuration, at block 1015, a determination may be made as to whether the contact between the user's skin and the electrodes is maintained. For example, the polling module 405 may poll the coupled electrodes to determine whether the flow of current between the electrodes is greater than zero. If it is determined that the contact is maintained (i.e., flow of current is greater than zero), physiological data may be collected by the coupled electrode tiles of the first AEA at block 1020. The electrodes may include biosensors to collect the data. The method 1000 may then return to determine whether the contact persists by continuing to poll the coupled electrodes. If, however, it is determined that the contact is terminated, the at least two adjacent electrode tiles may be decoupled at block 1025. The uncoupled electrodes may cease to collect physiological data associated with the user. The method 1000 may then return to continue to detect whether adjacent electrodes are in contact with the user's skin.

Therefore, the method 1000 may determine whether contact is maintained between electrode tiles and the skin of the user. It should be noted that the method 1000 is just one implementation and that operations of the method 1000 may be rearranged or otherwise modified such that other implementations are possible.

Figure 11:
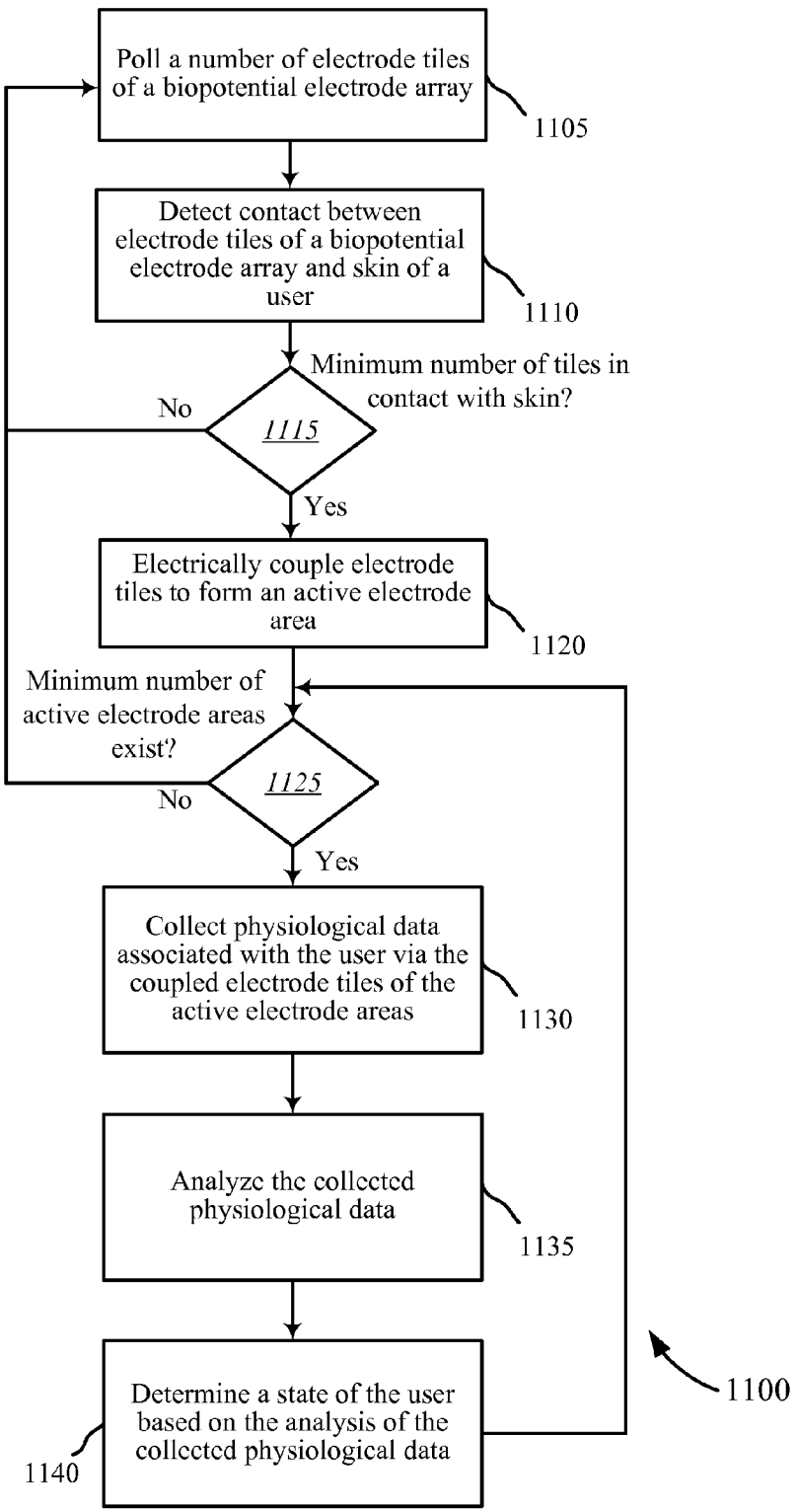
FIG. 11 is a flow chart illustrating one example of a method to poll electrode tiles of a dynamically configurable biopotential electrode array to detect contact between skin of a user and at least two of the electrodes.

Referring now to FIG. 11, a flow chart illustrates one example of a method 1100 to poll electrode tiles of a dynamically configurable biopotential electrode array to detect contact between skin of a user and at least two of the electrodes. The method 1100 may be implemented by a mobile device, such as the mobile device 115 of FIG. 1, 2, 3, 4, 5, 6, or 8. In one configuration, the method 1100 may be implemented by the detection module 210-*b*, the coupling module 215-*b*, the collection module 220-*b*, the polling module 405, the analysis module 410, and the state module 415 of FIG. 4.

At block 1105, a number of electrode tiles of a biopotential electrode array may be polled. For example, the current flow between adjacent electrodes may be polled to determine whether the flow is greater than zero. In one configuration, the array may be embedded on an external surface area of the mobile device 115. At block 1110, contact between electrode tiles and the skin of a user of the mobile device 115 may be detected. At block 1115, a determination may be made as to whether a minimum number of electrodes are in contact with the skin. If it is determined that a minimum number of electrodes are not in contact with the user's skin, the method 1100 may return to continue to poll electrode tiles to detect contact. If, however, it is determined that a minimum number of electrodes are in contact with the skin, at block 1120, the electrode tiles in contact with the skin may be electrically coupled to form an AEA.

At block 1125, a determination may be made as to whether a minimum number of AEAs exist. For example, certain types of physiological data may be gathered from a minimum number of AEAs. As an example, to collect GSR data, at least two AEAs may be used, while at least three AEAs may be used to collect electrocardiogram data. If it is determined that a minimum number of AEAs do not exist to collect the desired physiological data, the method 1100 may return to poll electrodes within the array to detect contact. If, however it is determined that a minimum number of AEAs exist, at block 1130, the physiological data may be collected via the electrodes of the AEAs. While the data is being collected, the polling module 405 may continue to poll electrodes in real time in order to detect whether the contact is maintained between the currently coupled electrodes as well as whether contact is detected between the skin and previously uncoupled electrodes.

At block 1135, the collected data may be analyzed. At block 1140, a state of the user may be determined based on the analysis. For example, an emotional state, a state of physical health, etc. of the user may be determined based on the analyzed physiological data. The method 1100 may return to determine whether the minimum number of AEAs still exists. If the AEAs are maintained, physiological data may continue to be collected via biosensors associated with the electrodes in the AEAs.

Therefore, the method 1100 may poll electrode tiles of a dynamically configurable biopotential electrode array to detect contact between skin of a user and the electrode tiles. It should be noted that the method 1100 is just one implementation and that operations of the method 1100 may be rearranged or otherwise modified such that other implementations are possible.

As provided by the description above, a biopotential array of electrode tiles may be embedded on an external surface area of the mobile device 115. The electrodes may be associated with biosensors used to collect physiological data relating to a user of the mobile device 115. The electrodes may be decoupled from each other until they come into contact with the user's skin. Decoupled electrodes may not be activated to collect physiological data associated with a user of the device 115. When contact is detected, an electronic switch between adjacent electrodes may close, thus electrically coupling the electrodes in contact with the skin. The biosensors associated with these coupled electrodes may then begin to collect physiological data about the user. As the user changes his/her grip of the mobile device 115 and touches different portions of the array, the coupled electrodes may be decoupled if contact with the skin does not persist. Previously uncoupled electrodes, that may now be in contact with the skin, may be electrically coupled to begin collecting the data.

The detailed description set forth above in connection with the appended drawings describes exemplary embodiments and does not represent the only embodiments that may be implemented or that are within the scope of the claims. The term "exemplary" used throughout this description means "serving as an example, instance, or illustration," and not "preferred" or "advantageous over other embodiments." The detailed description includes specific details for the purpose of providing an understanding of the described techniques. These techniques, however, may be practiced without these specific details. In some instances, well-known structures and devices are shown in block diagram form in order to avoid obscuring the concepts of the described embodiments.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, multiple microprocessors, one or more microprocessors in conjunction with a DSP core, or any other such configuration.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C).

Computer-readable media includes both computer storage media and communication media including any medium that facilitates transfer of a computer program from one place to another. A storage medium may be any available medium that can be accessed by a general purpose or special purpose computer. By way of example, and not limitation, computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk and blu-ray disc where disks usually reproduce data magnetically, while discs reproduce data optically with lasers. Combinations of the above are also included within the scope of computer-readable media.

The previous description of the disclosure is provided to enable a person skilled in the art to make or use the disclosure. Various modifications to the disclosure will be readily apparent to those skilled in the art, and the generic principles defined herein may be applied to other variations without departing from the spirit or scope of the disclosure. Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

What is claimed is:

1. A method to collect physiological data using a dynamically configurable biopotential electrode array, comprising:
    detecting contact between at least two contiguous electrode tiles of the biopotential electrode array and skin of a user;
    electrically coupling the at least two contiguous electrode tiles, based on detecting contact, to form a first active electrode area within the biopotential electrode array, the first active electrode area functioning as a single electrode; and
    collecting physiological data associated with the user via the coupled electrode tiles of the first active electrode area; and, wherein the contiguous electrode tiles share a border.

2. The method of claim 1, further comprising:
    polling the at least two electrically coupled electrode tiles within the first active electrode area to detect whether the contact between the at least two contiguous electrode tiles and the skin of the user is maintained.

3. The method of claim 2, further comprising:
    decoupling the at least two contiguous electrode tiles after contact between the skin of the user and the at least two contiguous electrode tiles is terminated.

4. The method of claim 1, further comprising:
    polling, concurrently with collecting the physiological data, a plurality of non-coupled electrode tiles of the biopotential electrode array to detect contact between non-coupled electrode tiles of the plurality of electrode tiles and the skin of the user.

5. The method of claim 4, further comprising:
    electrically coupling at least two contiguous electrode tiles, based on detecting contact, to form a second active electrode area within the biopotential electrode array, the second active electrode area functioning as a single electrode; and
    collecting physiological data associated with the user via the coupled electrode tiles of the second active electrode area.

6. The method of claim 5, wherein,
    the first active electrode area and the second active electrode area exist nonconcurrently within the biopotential electrode array.

7. The method of claim 1, further comprising:
    determining whether a minimum number of active electrode areas exist within the biopotential electrode array; and
    collecting physiological data associated with the user based on the determination that the minimum number of active electrode areas exist.

8. The method of claim 1, further comprising:
    detecting a plurality of active electrode areas within the biopotential electrode array;
    comparing signal qualities associated with each of the plurality of active electrode areas; and
    selecting at least one of the plurality of active electrode areas to collect physiological data based on the comparison of signal qualities.

9. The method of claim 1, wherein,
    the at least two electrode tiles comprise one or more biosensors to collect the physiological data.

10. The method of claim 9, wherein,
the one or more biosensors comprise an electrocardiogram (ECG) sensor or a galvanic skin response (GSR) sensor.

11. The method of claim 1, further comprising:
analyzing the collected physiological data associated with the user; and
determining a state of the user based on the analysis of the collected physiological data.

12. The method of claim 1, wherein,
the biopotential electrode array is embedded on a surface area of a handheld electronic device.

13. A communications device configured to collect physiological data using a dynamically configurable biopotential electrode array, comprising:
the biopotential electrode array;
a detection module configured to detect contact between at least two contiguous electrode tiles of the biopotential array and skin of a user;
a coupling module configured to electrically couple the at least two contiguous electrode tiles, based on detecting contact, to form a first active electrode area within the biopotential electrode area, the first active electrode area configured to function as a single electrode; and
a collection module configured to collect physiological data associated with the user via the coupled electrode tiles of the first active electrode area; and, wherein the contiguous electrode tiles share a border.

14. The communications device of claim 13, further comprising:
a polling module configured to poll the at least two electrically coupled electrode tiles within the first active electrode area to detect whether the contact between the at least two contiguous electrode tiles and the skin of the user is maintained.

15. The communications device of claim 14, wherein,
the coupling module is further configured to decouple the at least two continuous electrode tiles after contact between the skin of the user and the at least two continuous electrode tiles is terminated.

16. The communications device of claim 14, wherein, the polling module is further configured to poll, concurrently with collecting the physiological data, a plurality of non-coupled electrode tiles of the biopotential electrode array to dected contact between non-coupled electrode tiles of the plurality of electrode tiles and the skin of the user.

17. The communications device of claim 16, wherein,
the coupling module is further configured to electrically couple at least two continuous electrode tiles, based on detecting contact, to form a second active electrode area within the biopotential electrode array, the second active electrode area configured to function as a single electrode; and
the collection module is further configured to collect physiological data associated with the user via the coupled electrode tiles of the second active electrode area.

18. The communications device of claim 17, wherein,
the first active electrode area and the second active electrode area exist nonconcurrently within the biopotential electrode array.

19. The communications device of claim 13, wherein,
the collection module is further configured to determine whether a minimum number of active electrode areas exist within the biopotential electrode array; and
the collection module being further configured to collect physiological data associated with the user based on the determination that the minimum number of active electrode areas exist.

20. The communications device of claim 13, further comprising a comparing module and a selection module, wherein,
the detection module is further configured to detect a plurality of active electrode areas within the biopotential electrode array;
the comparing module is configured to compare signal qualities associated with each of the plurality of active electrode areas; and
the selection module is configured to select at least one of the plurality of active electrode areas to collect physiological data based on the comparison of signal qualities.

21. The communications device of claim 13, wherein,
the at least two electrode tiles comprise one or more biosensors to collect the physiological data.

22. The communications device of claim 21, wherein,
the one or more biosensors comprise an electrocardiogram (ECG) sensor or a galvanic skin response (GSR) sensor.

23. The communications device of claim 13, further comprising an analysis module and a state module, wherein,
the analysis module is configured to analyze the collected physiological data associated with the user; and
the state module is configured to determine a state of the user based on the analysis of the collected physiological data.

24. The communications device of claim 13, wherein,
the biopotential electrode array is embedded on a surface area of the communications device.

25. A system configured to collect physiological data using a dynamically configurable biopotential electrode array, comprising:
means for detecting contact between at least two contiguous electrode tiles of the biopotential electrode array and skin of a user;
means for electrically coupling the at least two contiguous electrode tiles, based on detecting contact, to form a first active electrode area within the biopotential electrode array, the first active electrode area configured to function as a single electrode; and
means for collecting physiological data associated with the user via the coupled electrode tiles of the first active electrode area; and, wherein the contiguous electrode tiles share a border.

26. The system of claim 25, further comprising:
means for polling the at least two electrically coupled electrode tiles within the first active electrode area to detect whether the contact between the at least two contiguous electrode tiles and the skin of the user is maintained.

27. The system of claim 26, further comprising:
means for decoupling the at least two contiguous electrode tiles after contact between the skin of the user and the at least two contiguous electrode tiles is terminated.

28. The system of claim 25, further comprising:
means for polling, concurrently with collecting the physiological data, a plurality of non-coupled electrode tiles of the biopotential electrode array to detect contact between non-coupled electrode tiles of the plurality of electrode tiles and the skin of the user.

29. The system of claim 28 further comprising:
means for electrically coupling at least two contiguous electrode tiles, based on detecting contact, to form a second active electrode area within the biopotential electrode array, the second active electrode area configured to function as a single electrode; and means for collecting physiological data associated with the user via the coupled electrode tiles of the second active electrode area.

30. The system of claim 29, wherein,
the first active electrode area and the second active electrode area exist nonconcurrently within the biopotential electrode array.

31. The system of claim 25, further comprising:
means for determining whether a minimum number of active electrode areas exist within the biopotential electrode array; and
means for collecting physiological data associated with the user based on the determination that the minimum number of active electrode areas exist.

32. The system of claim 25, further comprising:
means for detecting a plurality of active electrode areas within the biopotential electrode array;
means for comparing signal qualities associated with each of the plurality of active electrode areas; and
means for selecting at least one of the plurality of active electrode areas to collect physiological data based on the comparison of signal qualities.

33. The system of claim 25, wherein,
the at least two electrode tiles comprise one or more biosensors to collect the physiological data.

34. The system of claim 33, wherein,
the one or more biosensors comprise an electrocardiogram (ECG) sensor or a galvanic skin response (GSR) sensor.

35. The system of claim 25, further comprising:
means for analyzing the collected physiological data associated with the user; and
means for determining a state of the user based on the analysis of the collected physiological data.

36. A computer program product configured to collect physiological data using a dynamically configurable biopotential electrode array, the product comprising a non-transitory computer-readable medium, the medium comprising:
code to detect contact between at least two continuous electrode tiles of the biopotential electrode array and skin of a user;
code to electrically couple the at least two continuous electrode tiles, based on detecting contact, to form a first active electrode area within the biopotential electrode array, the first active electrode area configured to function as a single electrode; and
code to collect physiological data associated with the user via the coupled electrode tiles of the first active electrode area; and, wherein the contiguous electrode tiles share a border.

37. The computer program product of claim 36, wherein the medium further comprises:
code to poll the at least two electrically coupled electrode tiles within the first active electrode area to detect whether the contact between the at least two continuous electrode tiles and the skin of the user is maintained.

38. The computer program product of claim 37, further comprising:
code to decouple the at least two continuous electrode tiles after contact between the skin of the user and the at least two continuous electrode tiles is terminated.

* * * * *